United States Patent [19]
Villadsen et al.

[11] 3,960,665
[45] June 1, 1976

[54] PRODUCTION OF PROTEOLYTIC ENZYMES

[75] Inventors: Karl Johan Stampe Villadsen, Brabrand; Karin Pinholt Vestberg, Arhus, both of Denmark

[73] Assignee: Karl Johan Stampe Villadsen, Brabrand, Denmark

[22] Filed: July 2, 1973

[21] Appl. No.: 376,050

[30] Foreign Application Priority Data
July 7, 1972 United Kingdom.............. 31865/72

[52] U.S. Cl.................................. 195/66 R; 195/65; 252/99
[51] Int. Cl.²......................................... C12D 13/10
[58] Field of Search...................... 195/62, 65, 66 R

[56] References Cited
UNITED STATES PATENTS

| | | | |
|---|---|---|---|
| 3,723,250 | 3/1973 | Aunstrup et al. | 195/62 |
| 3,827,938 | 8/1974 | Aunstrup et al. | 195/62 |
| 3,838,009 | 9/1974 | Fukumoto et al. | 195/65 |

*Primary Examiner*—Lionel M. Shapiro
*Attorney, Agent, or Firm*—Lawrence Rosen; E. Janet Berry

[57] ABSTRACT

The invention relates to the production of proteolytic enzymes by aerob submerse fermentation of a *Bacillus firmus* var. Arosia, and to the use of the enzymes in detergent compositions containing perborates and polyphosphates.

7 Claims, No Drawings

PRODUCTION OF PROTEOLYTIC ENZYMES

This invention relates to the production of proteolytic enzymes by means of bacteriae, to the enzymes thus produced, and to the use of such enzymes in detergent compositions and the like.

Proteolytic enzymes are extensively used for improving the cleaning effect of detergent and the like compositions, particularly of the heavy duty kind.

Owing to the strongly alkaline conditions prevailing in solutions of the detergent compositions, the enzymes used in such compositions should be stable at fairly high alkaline pH-values, and most of the hitherto used enzymes of bacterial origin are, therefore, produced by means of bacteriae isolated from alkaline environments.

Thus in a known method, proteolytic enzymes for use in detergent compositions are produced by fermenting bacteriae of the genus Bacillus, which will grow at a pH between 9 and 11, in a suitable alkaline fermentation medium, and recovering the thus produced proteolytic enzymes.

However, even the proteolytic enzymes recovered in this manner, although fairly stable in washing lyes with a pH up to 11, will rapidly loose activity in the presence of perborates and polyphosphates, which form parts of most detergent compositions, and thus a need exists for proteolytic enzymes, which are stable at hightly alkaline pH-values in the presence of perborates and polyphosphates.

The present invention is based on the discovery that a microorganism of the genus Bacillus, which has been found in a sample of sea water from the Pacific Ocean, is able to produce a proteolytic enzyme or mixture of enzymes which is strongly active not only at high alkalinity but also in the presence of the perborates and polyphosphates usually present in detergent compositions.

This microorganism shows the following characteristic data:

Rods 0.7 × 2 – 10$\mu$. Gram-variable to Gram positive, curved, ends rounded.

Motile with peritrichous flagella. Rods occurring singly or in short chains. Rods stain uniformly, no vacuoles.

Spores oval-cylindrical, central-subterminal, not bulging rods, only produced on soya bean media. Ghosts are formed.

Colonies butyrous-waxy, raised, round, smooth-whitish, not pigmented. Agar slants smooth, flat, opaque. Colonies on soya bean media slightly wrinkled with finely dentate margins. No growth or very slight growth on glucose agar media.

Gelatine stab: slow stratiform - to crateriform liquefaction. Gelatine agar streak plate: Moderate zone of hydrolysis (2 days). Milk agar streak plate: no hydrolysis. Litmus milk unchanged. Blood agar: no haemolysis.

Broth: light flocculent turbidity with friable pellicle and slight ring-formation. Formation of tough vortex. Good growth on 5% NaCl.

Potato: no growth. Indole not produced. No acid or gas from glucose or other sugars. Ammonium salt not utilized as sole source of nitrogen. Starch hydrolyzed. Acetyl methylcarbinol not produced. very little growth in glucose broth. Citrates are weakly utilized. Nitrites produced and a few bubbles of $N_2$ in semisolid nitrate medium. Urease not produced. Aerobic, oxidase positive.

As compared with the genera of the family Bacillaceae described in Bergey's Manual of Determinative Bacteriology, 7th ed. (1957) the above microorganism is more like Bacillus firmus than any other of the described species, but varies from the former in respect of utilization of citrate and of hydrolysis of casein. It has, therefore, been named *Bacillus firmus var. Arosia*, and a culture has been deposed at the National Collection of Industrial Bacteriae in Aberdeen under No. 10557.

Thus, the method according to the invention is characterized in that a strain of Bacillus firmus var. Arosia is fermented under aerobic conditions in a suitable medium, the resulting proteolytic enzymes being recovered from the fermentation solution.

In the following, the fermentation and preferred conditions and media therefore will be described more detailed and with illustrative examples.

The incubation of the microorganism may take place in a soy bean agar medium, preferably at pH 10, even if a higher or lower pH may also be used. A suitable period of incubation is 24 hours at 37°C.

The further propagation takes place in a larger container in usual manner by aerob submerse fermentation in a medium containing carbohydrates, examples of which are lactose, saccharose, dextrin, and starch from potatoes and barley, nitrogen compounds as, for example, nitrates, ammonium salts, urea, soy protein, and casein, and phosphates as, for example, sodium and potassium phosphates and polyphosphates, together with buffering substances, traces of useful heavy metal compounds, and other usual adjuvants.

The following example is illustrative of a suitable aqueous fermentation medium and conditions for propagation purposes.

EXAMPLE 1

| | |
|---|---|
| Dextrin | 2.5% |
| Defatted soy meal | 5.5% |
| Saccharose | 3.0% |
| Sodium carbonate | 0.9% |
| Sodium hydrogen carbonate | 0.3% |
| Trisodium polyphosphate | 0.3% |
| Temperature | 28–50°C, preferably 35–40°C |
| Time | 40–100 hours, preferably 50–70 hours |
| Aeration | ¼–1 vol. air/vol. liquid, preferably ½ vol. air/vol. liquid, per minute |

The main fermentation takes place in an aqueous fermentation medium containing the same ingredients as the propagation medium with a possible addition of an antifoaming agent.

The following examples are illustrative of media ingredients and fermentation conditions in the main fermentation.

EXAMPLE 2

The aqueous fermentation medium contains in 100 cubic meters:

| | | |
|---|---|---|
| Corn | 3,500 | kilograms |
| Defatted soy meal | 5,500 | — |
| Saccharose | 3,000 | — |
| Sodium carbonate | 900 | — |
| Sodium hydrogen carbonate | 300 | — |

-continued

| | |
|---|---|
| Trisodium polyphosphate | 185 — |

The buffering salts are sterilized separately and added under sterile conditions after sterilization of the main portion. The fermentation conditions are:

| | |
|---|---|
| Temperature | 37°C |
| Time | 65 hours |
| pH | 7.5–10, approximately |
| Aeration | 0.5 vol air per vol liquid per minute |

The fermentation resuls in an enzyme production of about 250 Anson units per liter fermented medium as measued at 55°C and pH 9.

Instead of using buffering salts for controlling the pH value, it can also be controlled by means of adding acids or alkaline substances as necessary.

EXAMPLE 3

In a further embodiment of the main fermentation as set forth in Example 2, there are added 5000 kilograms of dextrin in 25 cubic meters of water during the fermentation period to stimulate the enzyme production and to prolong the production period. This results in a correspondingly larger yield of enzyme, since the fermented medium also in this case contains about 250 Anson units per liter.

The produced enzyme then has to be recovered. The first step in this process is a filtration of the fermented medium to separate the microorganisms. If desired, the filtrate may then be concentrated to a smaller volume, e.g. to one fourth of its original volume, before the next step, consisting in a precipitation of the enzyme. Before the precipitation, the liquid may be sterile filtered to remove spores or germs or, if preferred, the sterilization may be performed by irradiation of the final enzyme product.

The precipitation is carried out by adding of either a water-miscible organic solvent or an inorganic salt, such as sodium sulphate or ammonium sulphate to the filtrate.

The precipitate is separated as a slurry which is centrifuged, after which the solid matter is dried in any convenient manner, for instance by flashdrying, spraydrying, fluid bed drying or a combination of said drying methods as usually applied.

The filtration step is made easier by subjecting the fermented medium to a flocculation beforehand. The following examples are illustrative of flocculation agents for this purpose.

EXAMPLE 4

To 1000 liters of fermented medium are added 20 kilograms of aluminium sulphate dissolved in 100 liters of water, followed by 10 kilorams of burnt lime suspended in 100 liters of water.

Instead of burnt lime, an equivalent amount of sodium hydroxide may be used.

EXAMPLE 5

To 1000 liters of fermented medium are added 25 kilograms of calcium chloride dissolved in 25 liters of water, followed by 3.5 kilograms of burnt lime in 15 liters of water.

The flocculated medium is then filtered and/or centrifuged to remove the flocked matter.

EXAMPLE 6

To precipitate the enzyme, 3500 liters of ethanol are added per 1000 liters of the filtered fermentation medium, and the precipitate is filtered or centrifuged off and dried.

EXAMPLE 7

Instead of using ethanol for the precipitation, 300 kilograms of sodium or ammonium sulphate per 1000 liters of filtered fermentation medium is used.

When burnt lime has been used for the flocculation, as in Examples 5 and 6, it may be desirable to remove a surplus of calcium before precipitating the enzyme. This can be done by adding a 5–10% aqueous solution in an amount equivalent to the content of calcium ions present, and removing the precipitated calcium sulphate by filtration.

The enzymatic activity of the enzymes produced according to the invention has been determined to ascertain the changes taking place when changing pH.

The determinations appearing from the following Table I were carried out in solutions containing 0.5% casein buffered to the desired pH by means of sodium borate to which were added enzymes to a strength of 0.04 Anson units per liter.

The mixture was then incubated for 15 minutes at 50°C, after which the reaction was stopped in a boiling water bath. The activity was then determined by measuring, at 420 nm, the amount of amino acids liberated by coupling with 2,4,6-trinitrobenzenesulphonic acid.

Table I

| pH | Relative Activity in % at Different pH-Values | Activity | |
|---|---|---|---|
| 7 | 58.5 | 92.5 | 83 |
| 8 | 100 | 158 | 142 |
| 9 | 63.2 | 100 | 90 |
| 10 | 70.6 | 111 | 100 |
| 11 | 58.5 | 92.5 | 83 |
| 12 | 53.5 | 84 | 76 |

The stability of the enzymatic preparations of the invention were determined as follows:

Enzymatic solutions were prepared with a strength of 1.5 Anson units per liter, and the pH was adjusted by means of 0.2M borate buffer. After standing for 30 minutes at 50°C, the pH of each of the solutions was readjusted to 9.4, and the remaining activity was determined as above. Table II below shows this remaining activity in percent of the original activity.

Table II

| pH | % Remaining Activity |
|---|---|
| 7 | 92 |
| 8 | 99 |
| 9 | 96 |
| 10 | 90 |
| 11 | 90 |
| 12 | 67 |

Next the stability of the enzymes was determined in solutions containing the enzymes together with the following salts individually or in combination as follows:

| | |
|---|---|
| Enzyme | 0.075 Anson units per liter (A/l) |
| Tripolyphosphate (TPP) | 2.5 grams per liter (g/l) |
| Sodium perborate (NaPB) | 1.25 grams per liter |

-continued

Sodium metasilicate (NaMS)     0.45 grams per liter

The residual activity was determined in solutions containing 0.5% casein at pH 10, and the solutions were left for 20 minutes at 50°C.

The results appear from Table II below:

Table III

| Enzyme | A/l | 0.075 | 0.075 | 0.075 |
|---|---|---|---|---|
| TPP | g/l | 2.5 | 2.5 | 2.5 |
| NaPB | g/l | 0 | 1.25 | 1.25 |
| NaMs | g/l | 0 | 0 | 0.45 |
| Residual activity (after 30 min/45°C/ pH 10) | | 92% | 85% | 76% |

The activity as determined by washing tests on a standard type of soiled fabric named Empa 116 was also ascertained in a washing lye containing per liter 0.075 Anson units of the enzyme (as determined at 37°C and pH 9), 2.5 grams of TPP, 0.25 grams of ethoxylated fatty alcohol (Nonipol CS 50), and 1.25 grams of sodium perborate. At pH 10 and after washing for 30 minutes, the temperatures varying from 30°C to 65°C, the activity percentages in the following Table IV were determined by reflection measurement, the maximum value at 55°C arbitrarily being chosen as 100 percent.

Table IV

| % Activity of the Maximum | |
|---|---|
| °C | % Activity |
| 30 | 50.2 |
| 40 | 63.2 |
| 50 | 86.5 |
| 55 | 100.0 |
| 60 | 87.0 |
| 65 | 50.8 |

Similarly, the activity was determined at varying pH-values, the results appearing from the following Table V, the activity at pH 9 being arbitrarily chosen as 100 percent.

Table V

| pH | % Activity |
|---|---|
| 8.0 | 88.0 |
| 9.0 | 100.0 |
| 10.0 | 97.1 |
| 10.3 | 88.0 |
| 11.0 | 77.1 |
| 11.4 | 59.4 |

The invention also comprises the use of the enzymatic preparations produced according to the present method in detergent compositions.

The following, non-limiting Examples 8–11 are illustrative of such use, the figures representing percentages by weight.

EXAMPLES 8–11

| | 8 | 9 | 10 | 11 |
|---|---|---|---|---|
| Anionic tenside | 8.0 | 10.0 | | |
| Nonionic tenside | 4.0 | 2.0 | 3.0 | 5.0 |
| Soap | 3.0 | 2.0 | | |
| Ethylenediaminetetraacetate | 0.5 | | | |
| Carboxymethylcellulose | 1.0 | 1.0 | | |
| Optical brightener | 0.3 | 0.3 | | |
| Sodium silicate (Na$_2$O:SiO$_2$) ( 1:2 ) | 6.0 | 8.0 | | |
| Sodium metasilicate | | | 20.0 | 30.0 |
| Trisodium polyphosphate | 40.0 | 35.0 | 40.0 | 50.0 |
| Sodium sulphate | 4.2 | 33.7 | 7.0 | 5.0 |
| Sodium perborate | 25.0 | | 10.0 | |
| Sodium hexametaphosphate | | | 20.0 | |
| Sodium carbonate | | | | 10.0 |
| Water | 8.0 | 8.0 | | |
| Total | 100.0 | 100.0 | 100.0 | 100.0 |

To each of these compositions is added the enzyme preparation of the invention in a proportion corresponding to 1–12 Anson units per kilogram, possibly together with other enzymes.

Example 8 represents a typical detergent composition for heavy duty, Example 9 is also for heavy duty, but without perborate, Example 10 is a typical composition for dish-cleaning purposes, and Example 11 is a composition suitable for heavy duty cleaning.

Examples of anionic tensides are the alkylaryl sulphonates, and as nonionic tensides, e.g. ethoxylated fatty alcohols are suitable.

We claim:

1. Process for the production of proteolytic enzymes by aerobic fermentation of a medium containing cabohydrates, comprising using *Bacillus firmus var. Arosia*, strain NCIB 10557, for the fermentation, and recovering the produced enzymes from the resulting fermentation liquid.

2. Process according to claim 1, in which the fermentation is carried out at a temperature between 28°C and 50°C for a period of 48 to 72 hours.

3. Process according to claim 1, in which the fermentation liquid is subjected to flocculation before recovering of the enzymes.

4. Process according to claim 3, in which the flocculation is performed by adding an inorganic salt to the fermented liquid.

5. Process according to claim 3, in which the flocculated liquid is filtrated, and the enzyme is precipitated by a salting out procedure.

6. Process according to claim 3, in which the flocculated liquid is filtered, and the enzyme is precipitated by admixing a water-miscible organic solvent to the filtrate.

7. Proteolytic enzymes as produced by the process according to claim 1.

* * * * *